(12) United States Patent
Mabry et al.

(10) Patent No.: US 7,455,072 B2
(45) Date of Patent: Nov. 25, 2008

(54) DEVICE FOR SELECTIVELY REGULATING THE FLOW RATE OF A FLUID

(75) Inventors: Eric Mabry, Trabuco Canyon, CA (US); Kenneth Wayne Rake, Laguna Niguel, CA (US)

(73) Assignee: I-Flow Corporation, Lake Forest, CA (US)

(*) Notice: Subject to any disclaimer, the term of this patent is extended or adjusted under 35 U.S.C. 154(b) by 482 days.

(21) Appl. No.: 10/527,782

(22) PCT Filed: Sep. 18, 2003

(86) PCT No.: PCT/US03/30135
§ 371 (c)(1),
(2), (4) Date: Mar. 11, 2005

(87) PCT Pub. No.: WO2004/026373
PCT Pub. Date: Apr. 1, 2004

(65) Prior Publication Data
US 2006/0070669 A1 Apr. 6, 2006

Related U.S. Application Data

(60) Provisional application No. 60/412,409, filed on Sep. 19, 2002.

(51) Int. Cl.
*A61M 39/28* (2006.01)
*F16K 7/06* (2006.01)
*A61M 5/168* (2006.01)

(52) U.S. Cl. ............ 137/599.06; 137/595; 251/297; 604/34; 604/250

(58) Field of Classification Search ............ 137/595, 137/599.05, 599.06, 599.07; 604/30, 34, 604/246, 250; 251/297
See application file for complete search history.

(56) References Cited

U.S. PATENT DOCUMENTS 3,298,367 A * 1/1967 Bergman .................. 604/246

(Continued)

FOREIGN PATENT DOCUMENTS

AU 492 047 B 4/1978

(Continued)

OTHER PUBLICATIONS

Examination Report on corresponding foreign application from the Intellectual Property Office of New Zealand dated Jun. 29, 2005.

(Continued)

*Primary Examiner*—John Rivell
(74) *Attorney, Agent, or Firm*—Klein, O'Neill & Singh, LLP

(57) ABSTRACT

A device for regulating the flow rate of a fluid includes a housing containing a plurality of flow conduits fluidly connecting an inlet and an outlet, each of the flow conduits comprising a flow control tube (310, 312, 314) and a resiliently compressive occlusion tube (316, 318, 320), wherein the flow control tubes are of substantially equal internal diameter. Each of the flow control tubes has a length associated with a different flow rate. A resilient flow-blocking element (212a, 212b, 212c) is operatively associated with each of the occlusion tubes and is movable into a flow-blocking compression against its associated occlusion tube. An actuation mechanism (206) in the housing is operable: (a) to selectively engage and move one or more of the flow-blocking elements into the flow-blocking compression against its associated occlusion tube, and (b) to selectively be disengaged from any of the flow-blocking elements.

21 Claims, 5 Drawing Sheets

U.S. PATENT DOCUMENTS

| | | | | |
|---|---|---|---|---|
| 3,878,869 | A * | 4/1975 | Yamanouchi et al. | 604/246 |
| 4,425,116 | A * | 1/1984 | Bilstad et al. | 137/595 |
| 4,742,848 | A * | 5/1988 | Black | 251/297 |
| 4,822,344 | A * | 4/1989 | O'Boyle | 604/246 |
| 4,950,255 | A * | 8/1990 | Brown et al. | 604/250 |
| 5,009,251 | A * | 4/1991 | Pike et al. | 137/599.06 |
| 5,113,906 | A * | 5/1992 | Hogner | 137/595 |
| 5,318,515 | A * | 6/1994 | Wilk | 604/30 |
| 5,584,320 | A * | 12/1996 | Skinkle et al. | 137/595 |
| 5,901,745 | A * | 5/1999 | Buchtel | 137/595 |
| 5,925,023 | A | 7/1999 | Hiejima | 604/246 |
| 6,367,502 | B1 | 4/2002 | Kanai et al. | 137/556 |
| 6,648,017 | B2 * | 11/2003 | Lamas et al. | 137/595 |
| 6,939,324 | B2 * | 9/2005 | Gonnelli et al. | 604/142 |

FOREIGN PATENT DOCUMENTS

DE 40 36 509 C1 2/1992

OTHER PUBLICATIONS

Examination Report on corresponding foreign application from The Patent Office of India dated Oct. 25, 2005.

Examination Report on corresponding foreign application from The Danish Office of Singapore dated Sep. 28, 2006.

Office Action on corresponding foreign application from the Canadian Intellectual Property Office dated Mar. 8, 2007.

Correspondence regarding an Office Action of Jun. 29, 2007 on the corresponding foreign application from the State Intellectual Property Office of the PRC.

Examination Report on corresponding foreign application from the Korean Patent Office dated Jul. 20, 2007.

Examiner's Report on corresponding foreign application (AU Application No. 2003275234) from the Australian Intellectual Property Office dated Sep. 20, 2007.

* cited by examiner

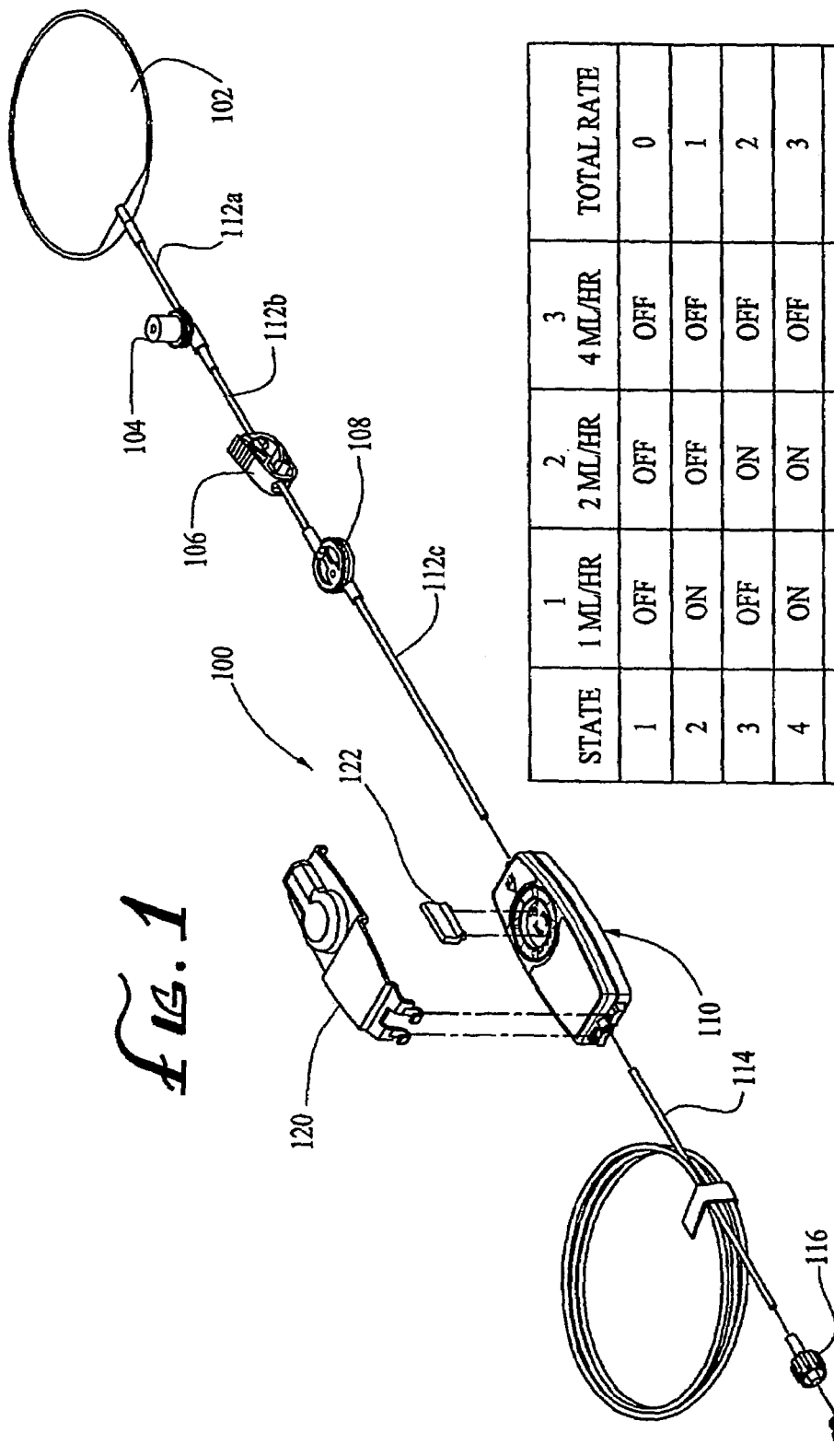

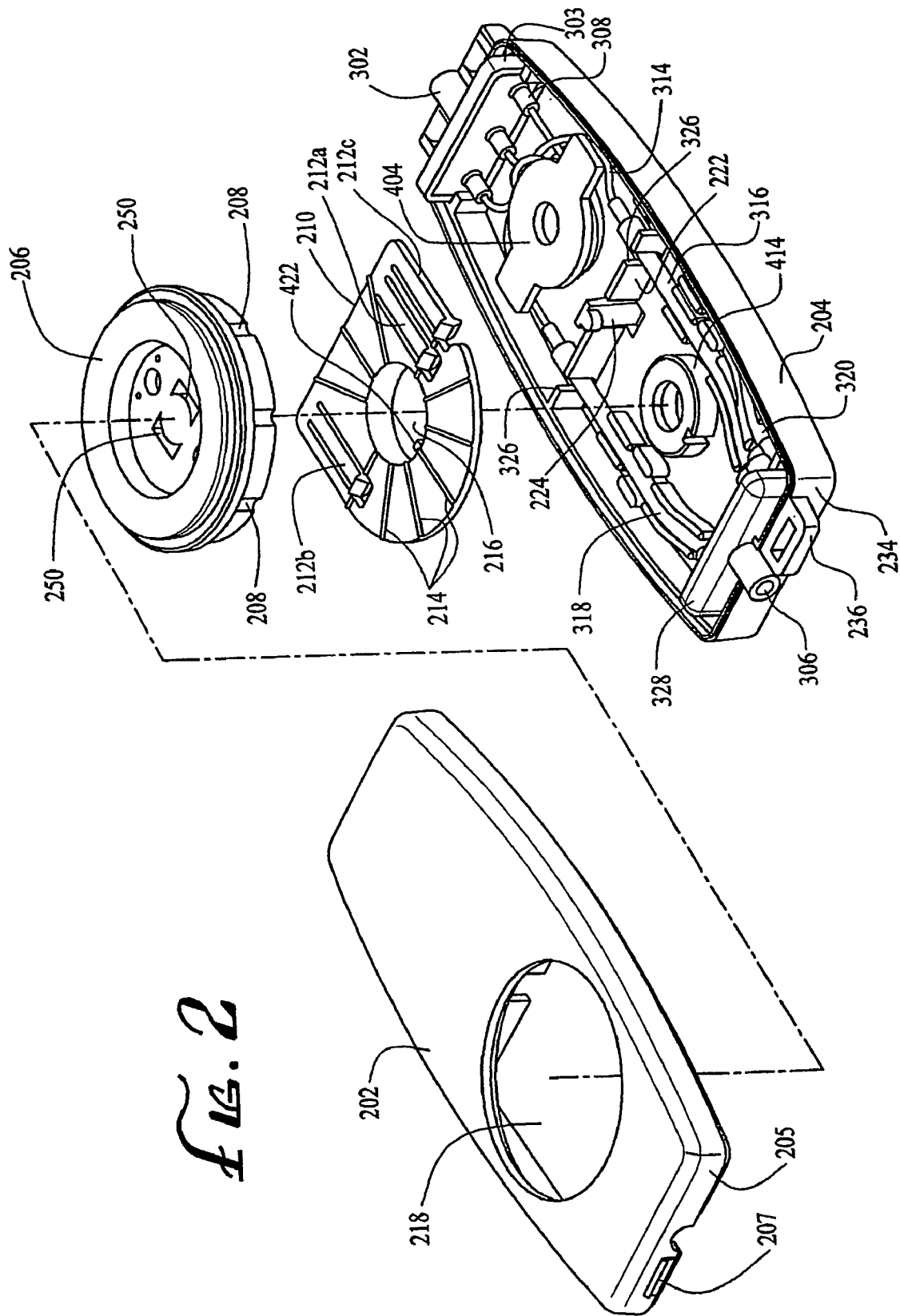

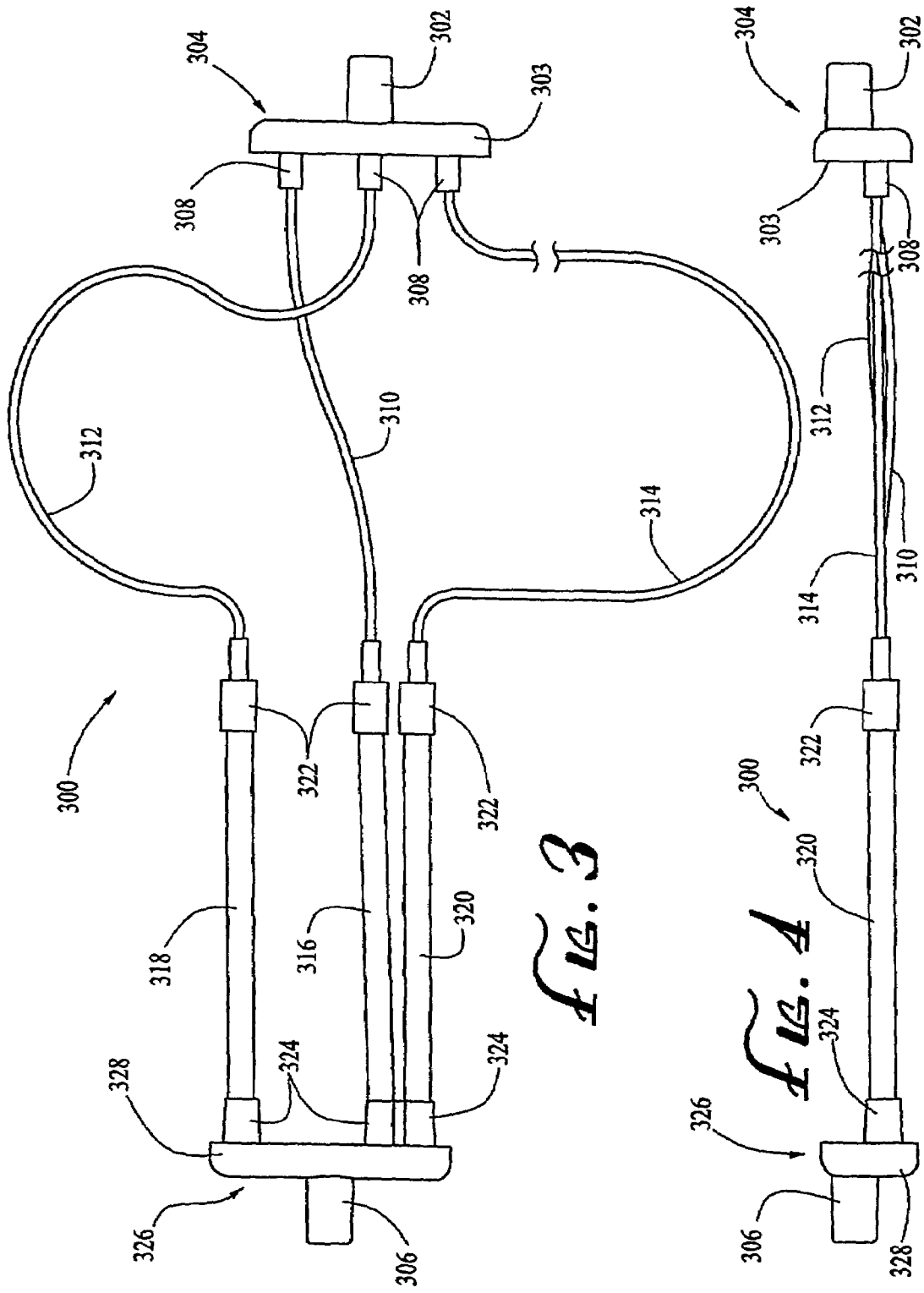

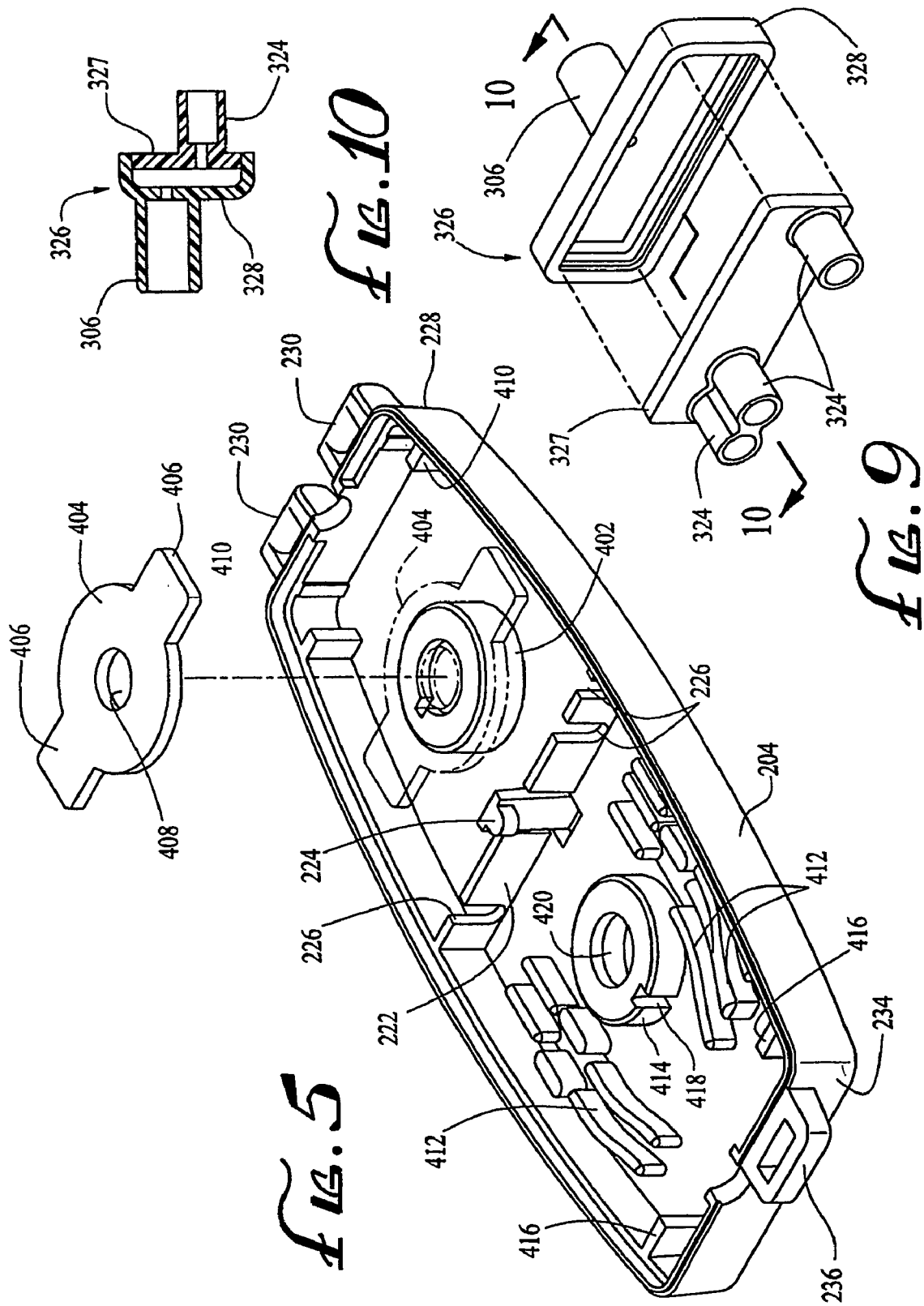

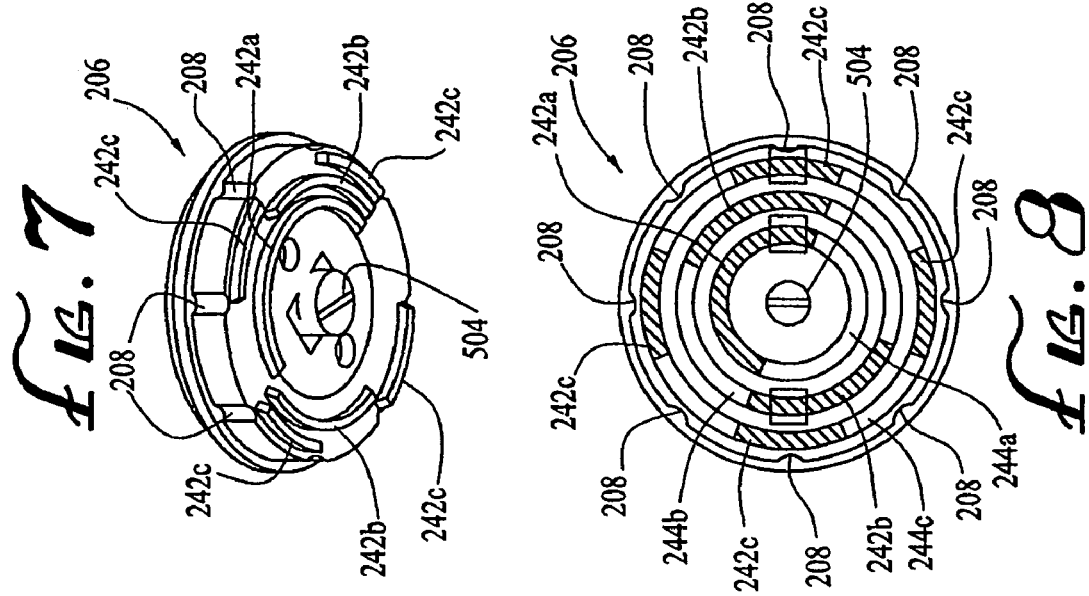
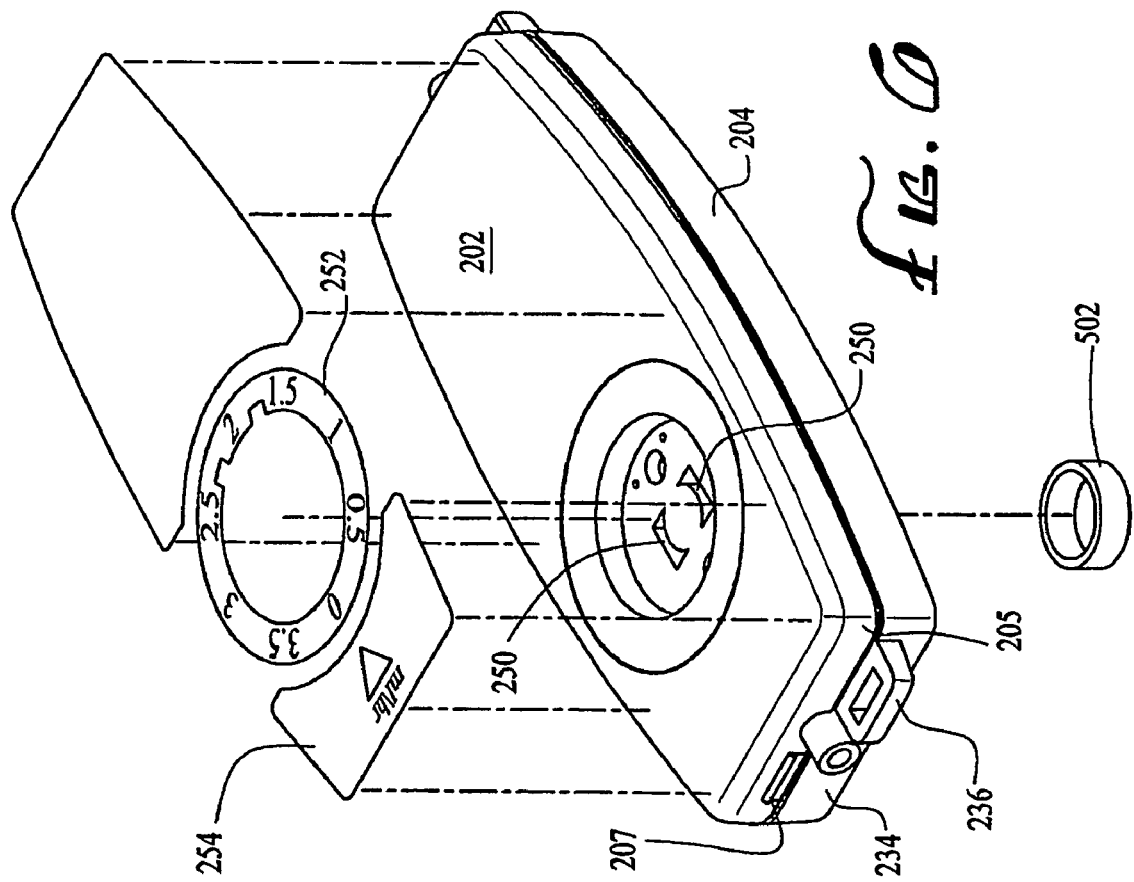

DEVICE FOR SELECTIVELY REGULATING THE FLOW RATE OF A FLUID

CROSS REFERENCE TO RELATED APPLICATION

This application claims the benefit, under 35 U.S.C. Section 119(e), of co-pending U.S. provisional application No. 60/412,409, filed 19 Sep. 2002, the disclosure of which is incorporated herein by reference.

FEDERALLY SPONSORED RESEARCH OR DEVELOPMENT

Not Applicable

BACKGROUND OF THE INVENTION

The present invention relates generally to devices for regulating the flow of intravenous fluids. More specifically, it relates to devices that permit the selection of any of a plurality of discrete flow rates for the continuous infusion of intravenous liquids.

In the medical field, therapeutic or medicinal liquids are often administered to a patient by intravenous (IV) infusion system. In an infusion system, the liquid is typically contained in a reservoir (a bag or a bottle) suspended above the patient, and delivered through a tube, by the force of gravity, to an IV needle inserted into the patient's vasculature. Alternatively, the liquid may be delivered from a reservoir by an infusion pump.

It is sometimes necessary to control the flow rate at which the liquid is delivered to the patient, particularly when the liquid is to be administered continuously over an extended period of time. The flow rate may be varied depending on, for example, the specific medical treatment, type of medicinal or therapeutic agent, or the specific needs of a particular patient. Indeed, a specific patient's need or demand for a particular drug or other agent may vary over time.

A variety of devices and techniques have been devised to control the flow rate of an IV-administered agent. For example, a clamp may be provided on the IV tubing to restrict the flow rate through the tubing. The technique does not, however, permit precise metering or control of the flow rate. Another device that purports to control the flow rate through an IV system is disclosed in U.S. Pat. No. 5,318,515—Wilk. In this device, a housing contains a plurality of flow control tubes of different cross-sectional areas that are connected to an inlet that receives the liquid from the reservoir through an inlet tube. A selector mechanism on the housing allows the flow path through one or more of the flow control tubes to be selectively opened to a housing outlet, which is connected by an outlet tube to the IV needle. By opening different combinations of the flow control tubes, any of a plurality of discrete flow rates can be selected. While this approach has shown promise, improvements have been sought that would provide more precise selection and control of fluid flow rates, in a device that is inexpensive to manufacture, and simple and reliable to use.

Thus, there has been a need for a device that allows the selection of any of a plurality of discrete flow rates in an IV system, and that also combines a relatively high degree of precision in the selected flow rate with ease of changing the selected flow rate. There has been a further need for a device in which the selected flow rate remains stable over time. In addition, such a device should be easy and inexpensive to manufacture, so that it may be economically made as a disposable item, while providing a high degree of reliability in use.

SUMMARY OF THE INVENTION

A device for selectively regulating the flow rate of a liquid, in accordance with the present invention, includes a plurality of flow control tubes, each of which is coupled between an inlet and one of a corresponding plurality of occlusion tubes. The flow control tubes, while being of equal cross-sectional area, are of different lengths, whereby the flow rate through each flow control tube is inversely proportional to its length. Each of the plurality of occlusion tubes is coupled between a corresponding one of the flow control tubes and an outlet. A flow control mechanism includes a plurality of flow-blocking elements, each of which is operable on a corresponding occlusion tube. An actuation mechanism moves corresponding flow blocking elements to close off flow through one or more of the occlusion tubes. The flow rate through the device thus depends on which of the flow control tubes is fluidly coupled to the outlet through its corresponding occlusion tube. One or more of the flow control tubes can thus be selected to achieve any of several pre-selected discrete flow rates.

As will be appreciated more fully from the detailed description that follows, the present invention offers precise control of a selectable flow rate in a device that is economical to manufacture, and that thus lends itself to realization in a disposable unit. Furthermore, a device in accordance with the present invention is simple and reliable to use. Moreover, by changing the cross-sectional areas of the flow control tubes, different ranges of flow rates can be provided, thus increasing the versatility of the device.

BRIEF DESCRIPTION OF THE DRAWINGS

FIG. 1 is a perspective, semi-exploded view of an I infusion system incorporating a selectable flow rate regulating device in accordance with the present invention;

FIG. 2 is an exploded perspective view of a selectable flow rate regulating device in accordance with a preferred embodiment of the present invention;

FIG. 3 is a top plan view of the flow control tube assembly used in a preferred embodiment of the present invention;

FIG. 4 is a side elevational view of the flow control tube assembly of FIG. 3;

FIG. 5 is a perspective view of the interior of the housing of the preferred embodiment of the invention;

FIG. 6 is a perspective view of the housing shown in FIG. 5, showing the housing with its cover attached;

FIG. 7 is a bottom perspective view of a cam that is employed as part of the actuation mechanism of the preferred embodiment;

FIG. 8 is a bottom perspective view of the cam of FIG. 7;

FIG. 9 is a perspective view of an outlet manifold that may be included in a preferred embodiment of the invention;

FIG. 10 is a cross-sectional view taken along line 10-10 of FIG. 9; and

FIG. 11 is a table showing an example of the flow rates that can be selected with various settings of an exemplary embodiment of the present invention.

DETAILED DESCRIPTION OF A PREFERRED EMBODIMENT

Referring to FIG. 1, an infusion system 100 is shown, in which a flow rate regulating device 110 in accordance with the present invention may be employed. The infusion system 100 includes a fluid reservoir 102, which may be a bag as shown. The reservoir bag 102 is typically pre-filled with a volume of a therapeutic liquid (e.g., a medicinal agent), and is of a known type that is advantageously pressurized by a pump (not shown) that controllably applies a positive pressure to the reservoir bag 102. The reservoir bag 102 is fluidly connected to the inlet of the regulating device 110 by an upstream IV line 112, which comprises several segments of flexible tubing cut to suitable lengths. A first segment 112a connects the outlet of the reservoir bag 102 with the inlet of a conventional fill valve 104. The fill valve 104 allows additional doses of a therapeutic agent (which may be something other than that with which the reservoir bag 102 is filled) to be administered as needed to the patient. A second segment 112b connects the outlet of the fill valve 104 with the inlet of a conventional filter 108, used for removing air and/or particulate contaminants from the fluid. A clamp 106 may be installed on the second segment 112b between the fill valve 104 and the filter 108, for selectively interrupting the flow from the reservoir bag 102. A third segment 112c connects the outlet of the filter 108 with the inlet of the regulating device 110.

A downstream IV line 114 is connected to the outlet of the regulating device 110, and terminates in a male Luer fitting 116. The Luer fitting 116 is of a type to which an IV catheter or other device (not shown) may be attached, as by a mating female Luer fitting (not shown), for introduction into the vasculature of the patient. When not in use, an end cap 118 may be installed on the male Luer fitting to prevent leakage.

The regulating device 110 is used to regulate and adjust the flow rate of the liquid delivered from the reservoir bag 102 to the patient. In some situations, it may be desired to prevent or deter unauthorized or unsupervised adjustments to the flow rate delivered by the regulating device 110. Accordingly, an optional security cover 120 and/or a removable key 122 may be provided for the regulating device 110. A lockable, tamper-resistant strap (not shown) can also be placed around the flow regulating device 110 with the security cover 120 in place to provide further impediments to unauthorized adjustments.

As will be described in more detail below, the flow regulating device 110 allows a medical practitioner, health care provider, or the patient himself/herself to adjust the rate of flow of the contents of the reservoir bag 102 to the patient. The device 110 includes an actuating mechanism, described below, that can be selectively moved to different positions, each corresponding to a discrete flow rate. The actuating mechanism causes the movement of one or more blocking devices to incrementally increase or decrease the flow rate through the device 110 by selectively obstructing fluid flow through one or more flow control tubes of equal internal diameter and unequal length. Thus, a set of discrete flow rates, from zero to a specified upper limit, can be provided with the device 110. The upper flow rate limit can be selected, for example, on the basis of the most likely maximum dosage for the therapeutic agent to be delivered.

FIG. 2 illustrates the major components of the flow regulating device 110. Specifically, the device includes an upper housing half 202 and a lower housing half 204. Mounted in the lower housing half 204 is a flow control mechanism, comprising a cam rotor 206 with peripheral grooves 208, and a cam follower plate 210 with a plurality of flow-blocking elements, which, in the preferred embodiment, comprise three resilient cam follower fingers 212a, 212b, 212c. A plurality of detent ridges 214 radiate from a central aperture 216 in the cam follower plate 210. The operation of the flow control mechanism will be described below.

FIGS. 3 and 4 illustrate a flow control tube assembly 300 that is installed in the lower housing half 204 to provide a plurality of selectable fluid flow paths, each having a predetermined flow rate, between the upstream IV line 112 and the downstream IV line 114, between which the flow regulating device 110 is installed.

The flow control tube assembly 300 includes an outlet manifold 304 comprising an outlet port 302 for fluid connection to the upstream end of the downstream IV line 114, an outlet plenum chamber 303, and a plurality (preferably three) of flow control tube connection ports 308. The respective downstream ends of a first flow control tube 310, a second flow control tube 312, and a third flow control tube 314 are each connected to one of the flow control tube connection ports 308, preferably by a solvent bond. The flow control tubes 310, 312, and 314 are preferably made of flexible extruded PVC.

Each of the flow control tubes 310, 312, 314 for a particular range of flow rates has approximately the same inside diameter. Specifically, tubes with inside diameters of about 0.003 to 0.004 in. (0.076 mm to 0.010 mm) may be used, but tubes having larger or smaller inside diameters can be used, depending on the range of flow rates desired, the range of flow rates for a given pressure being directly proportional to the inside diameter of the tubes. The flow control tubes 310, 312, and 314 are of different lengths, and for tubes of equal inside diameters and for any given applied fluid pressure, the flow rate through each of the tubes 310, 312, 314 is inversely proportional to its length. For example, in one specific embodiment, the lengths may respectively be 2 in. (51 mm), 4 in. (102 mm), and 8 in. (203 mm).

The upstream end of each of the flow control tubes 310, 312, 314 is fluidly coupled to the downstream end of a corresponding occlusion tube 316, 318, 320, respectively, the connections being preferably effected by solvent bonding to molded PVC coupling elements 322. The occlusion tubes 316, 318, 320 are preferably of substantially equal lengths and internal diameters. The occlusion tubes 316, 318, 320 are of a soft, flexible plastic material, preferably low shore hardness PVC, so that they are resiliently compressible. Thus, the first flow control tube 310 and its associated occlusion tube 316 form a first flow conduit, the second flow control tube 312 and its associated occlusion tube 318 form a second flow conduit, and the third flow control tube 314 and its associated occlusion tube 320 form a third flow conduit. The upstream ends of the occlusion tubes 316, 318, 320 are each connected, preferably by solvent bonding, to one of three occlusion tube connection ports 324 of an inlet manifold 326. The inlet manifold 326 includes an inlet port 306 that is adapted for fluid connection to the downstream end of the upstream IV line 112.

FIGS. 9 and 10 illustrate the inlet manifold 326 in detail. The occlusion tube connection ports 324 extend from a lid 327 that is attached (as by sonic welding) to the interior side of an inlet plenum body 328, thereby defining an inlet plenum chamber 330. The inlet port 306 extends upstream from the external side of the inlet plenum body 328.

As shown in FIGS. 2 and 6, the lower housing half 204 and the upper housing half 202 are constructed so as to be fastened to each other to form a housing that contains the internal components of the device. The fastening may be by any suitable means, such as adhesive bonding or sonic welding. Alternatively, the upper housing half 202 may be connected to the lower housing half 204 by means such as a snap-together attachment mechanism (not shown), if it is desired to allow the upper housing half 202 to be removable. The upper housing half 202 is provided with an aperture 218 that is dimensioned and located so as to allow access to the cam rotor 206. When the housing halves 202, 204 are fastened to each other, the housing so formed includes upstream and downstream ends having openings through which the inlet port 306 and the outlet port 302, respectively, extend. As shown in FIG. 2, the upper housing half 202 has an upstream end wall 205 that may be provided with a detent 207 for securing the optional security cover 120.

Referring to FIGS. 2 and 5, the lower housing half 204 is divided into a downstream portion and an upstream portion by a lateral support 222. The lateral support 222 is itself interrupted by an upstanding detent engagement member 224, the purpose of which will be described below. Three vertical slots 226 are provided in the lateral support 222, each of which receives one of the occlusion tubes 316, 318, 320. The lower housing half 204 has a downstream end wall 228. A pair of hinge elements 230 may be provided on the exterior of the downstream end wall 228 for the attachment of the above-mentioned security cover 120.

A spool 402 is located in the downstream portion of the lower housing half 204. A spool cap 404, having a pair of diametrically-opposed tabs 406 and a central aperture 408, is attached to the top of the spool 402. The flow control tubes 310, 312, 314 are wrapped around the spool 402 and are retained by the spool cap 404, to prevent kinking and stretching of the flow control tubes. A pair of opposed outlet manifold retention tabs 410 is provided near the downstream end wall 228 of the lower housing half 204, thereby defining a space between the retention tabs 410 and the downstream end wall 228 for holding the outlet manifold 304.

The upstream portion of the lower housing half 204 is provided with three guide channels 412, each of which is aligned with one of the slots 226 in the lateral support 222, and each of which is configured to hold one of the occlusion tubes 316, 318, 320 in position for selective occlusion by the flow control mechanism, as will be described below. Centrally located in the upstream portion of the lower housing half 204 is an annular pedestal 414, to which the cam follower plate 210 (described above) is attached.

The lower housing half 204 has an upstream end wall 234. Optionally, an apertured fitting 236 may be provided on the upstream end wall 234 for the attachment of a tie wrap or cable wrap (not shown) that can be attached once the optional security cover 120 is in place. A pair of opposed inlet manifold retention tabs 416 is provided in the upstream portion of the lower housing half 204 near the upstream end wall 234, thereby defining a space between the upstream end wall 234 and the retention tabs 416 for holding the inlet manifold 326.

The annular pedestal 414 includes a vertical alignment slot 418 in its outer periphery, and a central aperture or recess 420. As best shown in FIG. 2, the central aperture 216 of the cam follower plate 210 is dimensioned to fit around the outside of the annular pedestal 414. A key or tab 422 extends into the central aperture 216 of the cam follower plate 210, and it is dimensioned to be received in the alignment slot 418 of the pedestal 414, thereby assuring the proper circumferential alignment of the cam follower plate 210 with respect to the pedestal 414. When the cam follower plate 210 is properly aligned, the cam follower fingers 212a, 212b, 212c are properly positioned to engage the occlusion tubes 316, 318, 320, respectively, as will be described below. Alternatively, this alignment can be provided by having a pedestal with a non-circular outer periphery and a cam follower plate with a mating non-circular aperture.

As shown in FIG. 6, an annular retention collar 502 is installed within the central aperture 420 of the support pedestal 414. Referring to FIGS. 7 and 8, the cam rotor 206 has a central retaining post 504 depending from its lower surface that fits into the retention collar 502. The retaining post 504 is split so that it fits with a snap fit into the retention collar 502, and it is frictionally held in place with respect to the collar 502, so that the cam rotor 206 and the collar 502 rotate together within the aperture 420, while the cam rotor 206 is restrained from vertical movement.

The detailed structure of the cam rotor 206 is shown in FIGS. 6, 7, and 8. The cam rotor 206 is a disc-like structure having a peripheral edge with a plurality of vertical (axial) detent grooves 208 formed into it at predefined circumferential intervals. The detent grooves 208 define rotational positions that represent pre-selected flow rate settings, and they are engaged by the detent engagement member 224 to provide a palpable "feel" when a desired flow rate is selected. The lower surface of the cam rotor 206 is provided with a plurality of cam elements 242a, 242b, 242c, respectively formed as arcuate ridges located in three concentric annular bands 244a, 244b, 244c around the center of the cam rotor 206. The radially innermost band 244a includes a single arcuate cam element 242a that subtends approximately 180° of arc. The middle band 244b includes a pair of diametrically-opposed arcuate cam elements 242b, each subtending approximately 90° of arc. The radially outermost band 244c includes four arcuate cam elements 242c equidistantly spaced around the circumference of the band 244c, and each subtending approximately 45° of arc. The radial distance of each of the bands 244a, 244b, 244c from the center of the cam rotor 206 corresponds to the distance from the center of the cam rotor 206 of one of the cam follower fingers 212a, 212b, 212c. Thus, as the cam rotor 206 is rotated, the innermost cam element 242a presses against the cam follower finger 212a, urging it downwardly. Similarly, the middle cam elements 242b press against the cam follower finger 212b, and the outermost cam elements 242c press against the cam follower finger 212c, urging these cam follower fingers downwardly when they are so engaged by their associated cam elements. When the cam follower fingers are forced downwardly by their associated cam elements, they squeeze down upon and thus compressively occlude their associated occlusion tubes, thereby shutting off flow through that tube, and thus through the flow conduit comprising the occluded occlusion tube and its associated flow control tube. Movement of a cam element off of its associated cam follower finger allows the finger to resiliently spring back to its original position, out of a compressive engagement with its associated occlusion tube, thereby opening the occlusion tube to flow from its associated flow control tube, and thus opening the flow conduit comprising that occlusion tube and its associated flow control tube.

In the exemplary embodiment shown, the cam rotor 206 is provided with eight detent grooves 208, representing the eight pre-selected flow rates that can be provided with three flow control tubes 310, 312, 314 of different lengths (and thus three different flow rates), as described above. An exemplary table of selectable, predefined flow rates for a three-tube device is shown in FIG. 11. Thus, in the specific example shown, the shortest flow control tube provides a flow rate of 4 ml/hr, the intermediate length flow control tube provides a flow rate of 2 ml/hr, and the longest flow control tube provides a flow rate of 1 ml/hr. A flow rate of zero is provided by rotating the cam rotor 206 to position or "state" 1, in which every occlusion tube is closed by the depression of its associated cam follower finger. In position or state 2 of the cam rotor 206, the occlusion tubes associated with the two longer flow control tubes are blocked by the depression of their associated cam follower fingers by the associated cam elements. The resultant flow rate through the device is thus 1 ml/hr. In similar fashion, the total flow rate through the device can be further incremented from 2 ml/hr to 7 ml/hr by rotating the cam rotor 206 to its positions or states 3 through 8, respectively. In position or state 8, none of the occlusion tubes is blocked by the action of the cam elements and their associated cam follower fingers, thereby allowing flow through all of the flow rate control tubes, totaling 7 ml/hr.

The flow rate range of the device will be determined by several parameters, specifically, the lengths and inside diameters of the flow control tubes, and the pressure applied to the upstream side of the flow control tubes. Should a greater number of incremental flow rates be desired between zero and the maximum, more than three flow control tubes and associated occlusion tubes can be provided, with a commensurate increase in the number of cam elements and cam follower fingers.

After the actuation mechanism, including the cam rotor 206, is installed in the lower housing half 204, the upper housing half 202 is attached to the lower housing half 204, e.g., by adhesive bonding or sonic welding. As best shown in FIG. 6, the upper surface of the cam rotor 206 is exposed through the aperture 218 in the upper housing half 202. The upper surface of the cam rotor 206 is advantageously provided with one or more key slots 250, dimensioned and located so as to receive the above-mentioned key 122, thereby allowing the cam rotor 206 to be rotated to a different position only when the key 122 is properly inserted into the slot(s) 250. The upper surface of the cam rotor 206 is provided with appropriate indicia to indicate the discrete flow rates that may be selected by rotation of the cam rotor 206 to its several predefined rotational positions. The flow rate indicia may be provided by an annular decal 252, for example, or by directly marking the surface of the cam rotor 206. The upper surface of the upper housing half 202 is advantageously marked with an arrow or like indicator, which may be provided by a second decal 254, to indicate which of the flow rates has been selected.

While a preferred embodiment has been described herein, it will be appreciated that the above-described embodiment is exemplary only, and that a number of variations and modifications will suggest themselves to those skilled in the art. Some of these modifications and variations have been mentioned above. Others may include such features as the number, arrangement, and configuration of the cam elements and the cam follower elements, the detent mechanism, and even the provision of alternative mechanisms for selectively blocking flow through one or more of the flow control tubes. These and other modifications, variations, and other equivalents should be considered within the spirit and scope of the invention, as defined in the claims that follow.

What is claimed is:

1. A device for selectively regulating the flow rate of a fluid, comprising:
    a housing including an inlet and an outlet;
    a plurality of flow conduits fluidly connected between the inlet and the outlet, each of the flow conduits comprising a resiliently compressible occlusion tube having a length representative of a different pre-defined flow rate; and
    a flow rate selection mechanism, operatively mounted in the housing, for selectively obstructing fluid flow through the flow conduits, thereby to provide a flow rate from the inlet to the outlet corresponding to the combined flow rates of the unobstructed flow conduits, wherein the flow rate selection mechanism comprises:
    at least first, second, and third flow-blocking elements, each of which is operatively associated with one of the flow conduits, each flow-blocking element being selectively movable into and out of a flow-blocking compression against its associated occlusion tube; and
    an actuation mechanism operatively engageable with each of the flow-blocking elements and movable among a plurality of pre-defined positions in all but one of which it operatively engages one or more of the flow-blocking elements to block flow through the flow conduit associated with each of the operatively-engaged flow-blocking elements, and in one position of which it operatively engages none of the flow-blocking elements; wherein the actuation mechanism comprises a cam rotor rotatably mounted in the housing and having a plurality of cam elements disposed thereon in positions in which each of the cam elements may operatively engage and move one of the flow-blocking elements into a flow-blocking compression against its associated occlusion tube as the cam rotor is rotated, wherein the cam rotor is rotatable among a plurality of rotary positions, each of which is associated with a predefined fluid flow rate, and wherein the plurality of cam elements includes at least a first cam element engageable only with the first flow-blocking element, a pair of diametrically-opposed second cam elements engageable only with the second flow-blocking element, and a plurality of third cam elements engageable only with the third flow-blocking element.

2. The device of claim 1, wherein each of the first, second, and third flow-blocking elements comprises a resilient cam follower finger.

3. The device of claim 1, wherein the first cam element is an arcuate cam element subtending approximately 180 degrees of arc and located at a first radial distance from the center of the rotor, wherein each of the pair of second cam elements is an arcuate cam element subtending approximately 90 degrees of arc and is located at a second radial distance from the center of the rotor, wherein each of the plurality of third cam elements is an arcuate cam element subtending approximately 45 degrees of arc and is located at a third radial distance from the center of the rotor, and wherein the first radial distance is less than the third radial distance, and the second radial distance is between the first and third radial distances.

4. The device of claim 3, wherein the plurality of third cam elements comprises four equidistantly-spaced third arcuate cam elements.

5. An infusion system for delivering selectable flow rates of a therapeutic liquid to a patient, comprising:
    a pressurized reservoir containing a volume of the liquid and having an outlet; and
    a flow-regulating device having an inlet fluidly coupled to the outlet of the reservoir and an outlet coupled to an IV conduit;
    wherein the flow-regulating device comprises:
        a plurality of flow conduits fluidly connected between the inlet and the outlet, each of the flow conduits having a length representative of a different pre-defined flow rate, each of the flow conduits comprising a resiliently compressible occlusion tube; and
        a flow rate selection mechanism for selectively obstructing liquid flow through the flow conduits, thereby to provide a flow rate from the inlet to the outlet corresponding to the combined flow rates of the unobstructed flow conduits, wherein the flow rate selection mechanism is operable selectively to block liquid flow through (a) none of the flow conduits, and (b) one or more of the conduits, the flow rate selection mechanism comprising:

at least first, second, and third flow-blocking elements, each of which is operatively associated with one of the flow conduits; and an actuation mechanism that is operable for selectively actuating the flow-blocking elements to block flow through the flow conduit associated with each actuated flow-blocking element, wherein the actuation mechanism comprises a cam rotor having a plurality of cam elements, each of which is positioned operatively to move one of the flow-blocking elements into a flow-blocking compression against its associated occlusion tube as the rotor is rotated, and wherein the plurality of cam elements includes at least first cam element engageable only with the first flow-blocking element, a pair of diametrically-opposed second cam elements engageable only with the second flow-blocking element, and a plurality of third cam elements engageable only with the third flow-blocking element.

6. The infusion system of claim 5, further comprising a fill valve fluidly coupled between the outlet of the reservoir and the inlet of the flow-regulating device.

7. The infusion system of claim 5, wherein in the reservoir is pressurized by a pump applying a controllable pressure to the reservoir.

8. The infusion system of claim 5, wherein each of the flow-blocking elements comprises a resilient cam follower finger located so as to be operatively urged into a compressive engagement with one of the occlusion tubes when the cam follower finger is engaged by a cam element.

9. The infusion system of claim 5, wherein the cam rotor is rotatable among a plurality of rotary positions, each of which is associated with a predefined fluid flow rate.

10. The infusion system of claim 5, wherein the first cam element is an arcuate cam element subtending approximately 180 degrees of arc and located at a first radial distance from the center of the rotor, wherein each of the pair of second cam elements is an arcuate cam element subtending approximately 90 degrees of arc and is located at a second radial distance from the center of the rotor, wherein each of the plurality of third cam elements is an arcuate cam element subtending approximately 45 degrees of arc and is located at a third radial distance from the center of the rotor, and wherein the first radial distance is less than the third radial distance, and the second radial distance is between the first and third radial distances.

11. The infusion system of claim 10, wherein the plurality of third cam elements comprises four equidistantly-spaced third arcuate cam elements.

12. A device for regulating the flow of a liquid from a pressurized source, comprising:

a housing having an inlet and an outlet;

at least first, second, and third flow conduits in the housing fluidly connecting the inlet and the outlet, each of the flow conduits comprising a flow control tube and a resiliently compressive occlusion tube, wherein the first flow control tube has a first length associated with a first pre-defined flow rate, the second flow control tube has a second length associated with a second pre-defined flow rate, and the third flow control tube has a third length associated with a third pre-defined flow rate;

at least first, second, and third flow-blocking elements, each of which is operatively associated with one of the occlusion tubes and movable into a flow-blocking compression against its associated occlusion tube; and an actuation mechanism in the housing that is operable (a) to selectively engage and move one or more of the flow-blocking elements into the flow-blocking compression against its associated occlusion tube, and (b) selectively be disengaged from any of the flow-blocking elements, wherein the actuation mechanism is operatively engageable with each of the flow-blocking elements and is movable among a plurality of pre-defined positions in all but one of which it operatively engages one or more of the flow-blocking elements to block flow through the occlusion tube associated with each of the operatively-engaged flow-blocking elements, and in one position of which it operatively engages none of the flow-blocking elements, the actuation mechanism comprising:

a cam rotor rotatably mounted in the housing and having a plurality of cam elements, each of which is positioned operatively to move one of the flow-blocking elements into a flow-blocking compression against its associated occlusion tube as the rotor is rotated, and wherein the plurality of cam elements includes at least a first cam element engageable only with the first flow-blocking element, a pair of diametrically-opposed second cam elements engageable only with the second flow-blocking element, and a plurality of third cam elements engageable only with the third flow-blocking element.

13. The device of claim 12, wherein each of the flow-blocking elements comprises a resilient cam follower finger located so as to be operatively urged into a compressive engagement with one of the occlusion tubes when the cam follower finger is engaged by a cam element.

14. The device of claim 12, wherein the cam rotor is rotatable among a plurality of rotary positions, each of which is associated with a predefined fluid flow rate.

15. The device of claim 12, wherein the first cam element is an arcuate cam element subtending approximately 180 degrees of arc and located at a first radial distance from the center of the rotor, wherein each of the pair of second cam elements is an arcuate cam element subtending approximately 90 degrees of arc and is located at a second radial distance from the center of the rotor, wherein each of the plurality of third cam elements is an arcuate cam element subtending approximately 45 degrees of arc and is located at a third radial distance from the center of the rotor, and wherein the first radial distance is less than the third radial distance, and the second radial distance is between the first and third radial distances.

16. The device of claim 15, wherein the plurality of third cam elements comprises four equidistantly-spaced third arcuate cam elements.

17. A device for selectively regulating the flow rate of a fluid, comprising:

a housing including an inlet and an outlet;

a plurality of flow conduits fluidly connected between the inlet and the outlet, each of the flow conduits having a length representative of a different pre-defined flow rate, wherein each of the flow conduits includes a resiliently compressible occlusion tube; and a flow rate select on mechanism, operatively mounted in the housing, for selectively obstructing fluid flow through the flow conduits, thereby to provide a flow rate from the inlet to the outlet corresponding to the combined flow rates of the unobstructed flow conduits, wherein the flow rate selection mechanism comprises:

a resilient flow-blocking cam follower element operatively associated with each of the flow conduits, each flow-blocking element being selectively movable into and out of flow-blocking compression against its associated occlusion tube; and a cam rotor disc rotatably mounted in the housing and having a lower surface provided with a plurality of cam elements in radial positions in which each of the cam elements is operatively engageable with an associated one of the flow-blocking cam follower elements as the rotor is rotated through a plurality pre-defined rotational positions, each of the rotational positions being associated with a pre-defined fluid flow rate, wherein in all but one of the rotational positions the cam elements operatively engage at least one of the flow-blocking cam follower elements to move into a flow-blocking compression against its associated occlusion tube, and wherein in one pre-defined rotational position the cam elements operatively engage none of the flow-blocking cam follower elements.

18. The device of claim 17, wherein the housing includes a detent member, and wherein the cam rotor disc has a peripheral edge with a plurality of detent grooves defining the respective rotational positions when engaged by the detent member.

19. The device of claim 17, wherein each of the cam elements is positioned on the lower cam rotor disc surface so as to move one of the resilient elements in a flow-blocking compression against its associated occlusion tube.

20. A device for regulating the flow of a liquid from a pressurized source, comprising:

a housing having an inlet and an outlet;

at least first, second, and third flow conduits in the housing fluidly connecting the inlet and the outlet, each of the flow conduits comprising a flow control tube and a resiliently compressive occlusion tube, the first flow control tube having a first length associated with a first pre-defined flow rate, the second flow control tube having a second length associated with a second pre-defined flow rate, and the third flow control tube having a third length associated with a third pre-defined flow rate;

a resilient flow-blocking cam follower element operatively associated with each of the occlusion tubes and movable into a flow-blocking compression against its associated occlusion tube; and an actuation mechanism in the housing that is operable (a) to selectively engage and move one or more of the flow-blocking cam follower elements into the flow-blocking compression against its associated occlusion tube, and (b) to selectively be disengaged from any of the flow-blocking cam follower elements, wherein the actuation mechanism comprises a cam rotor disc rotatably mounted in the housing and having a lower surface provided with a plurality of cam elements in radial positions in which each of the cam elements is operatively engageable with an associated one of the flow-blocking cam follower elements as the rotor is rotated through a plurality of pre-defined rotation positions, each of the rotational positions being associated with a pre-defined fluid flow rate, wherein in all but one of the rotational positions the cam elements operatively engage one or more of the flow-blocking cam follower elements to block flow through the occlusion tube associated with each of the operatively-engaged flow-blocking elements, and wherein in one pre-defined rotational position the cam elements operatively engage none of the flow-blocking cam follower elements.

21. The device of claim 20, wherein the housing includes a detent member, and wherein the cam rotor disc has a peripheral edge with a plurality of detent grooves defining the respective rotational positions when engaged by the detent member.

\* \* \* \* \*